(12) United States Patent
Eini et al.

(10) Patent No.: US 6,994,863 B2
(45) Date of Patent: Feb. 7, 2006

(54) PHARMACEUTICAL AND COSMETIC CARRIER AND COMPOSITION FOR TOPICAL APPLICATION

(75) Inventors: Meir Eini, Ness Ziona (IL); Dov Tamarkin, Maccabim (IL)

(73) Assignee: Foamix Ltd., Ness Ziona (IL)

( * ) Notice: Subject to any disclaimer, the term of this patent is extended or adjusted under 35 U.S.C. 154(b) by 0 days.

(21) Appl. No.: 10/392,071

(22) Filed: Mar. 19, 2003

(65) Prior Publication Data

US 2003/0157138 A1 Aug. 21, 2003

Related U.S. Application Data

(62) Division of application No. 09/653,267, filed on Aug. 31, 2000.

(60) Provisional application No. 60/216,162, filed on Jul. 3, 2000.

(51) Int. Cl.
  *A61K 7/00* (2006.01)
  *A61K 7/48* (2006.01)
  *A61K 31/74* (2006.01)

(52) U.S. Cl. ............... 424/401; 424/78.03; 424/78.07; 424/78.05; 424/78.06; 424/434; 514/682; 514/724

(58) Field of Classification Search ............... 424/401, 424/78.03, 434, 78.07, 78.05, 78.06; 514/682, 514/724
See application file for complete search history.

(56) References Cited

U.S. PATENT DOCUMENTS

| 4,151,272 | A |   | 4/1979  | Geary et al. ............. 424/68 |
| 4,229,432 | A |   | 10/1980 | Geria |
| 4,661,524 | A | * | 4/1987  | Thomson et al. .......... 514/682 |
| 4,992,478 | A |   | 2/1991  | Geria |
| 5,719,197 | A |   | 2/1998  | Kanios et al. |
| 5,817,322 | A |   | 10/1998 | Xu ............................. 424/401 |
| 5,837,270 | A |   | 11/1998 | Burgess |
| 5,925,669 | A |   | 7/1999  | Katz et al. |
| 5,952,392 | A | * | 9/1999  | Katz et al. .................. 514/724 |
| 6,224,888 | B1 |  | 5/2001  | Vatter et al. |
| 6,348,229 | B1 |  | 2/2002  | Eini et al. .................... 426/611 |

FOREIGN PATENT DOCUMENTS

WO 98/18472 5/1998

* cited by examiner

*Primary Examiner*—Gary Kunz
*Assistant Examiner*—Mina Haghighatian
(74) *Attorney, Agent, or Firm*—Wilmer Cutler Pickering Hale and Dorr LLP

(57) ABSTRACT

A pharmaceutical or cosmetic carrier or composition for topical application characterized by rheological properties which render the carrier or composition semi-solid at rest and a liquid upon application of shear forces thereto. The composition or carrier are prepared by mixing 1–25 percent of a solidifying agent and 75–99 percent of a hydrophobic solvent, by weight, wherein at least one of them has therapeutic or cosmetic benefits, in the presence or absence of a biologically active substance.

29 Claims, 1 Drawing Sheet

Figure 1 - the effect of a Corticosteroid Composition in Corticosteroid Composition in a Psoriasis Patient
After 10 days TU-2100
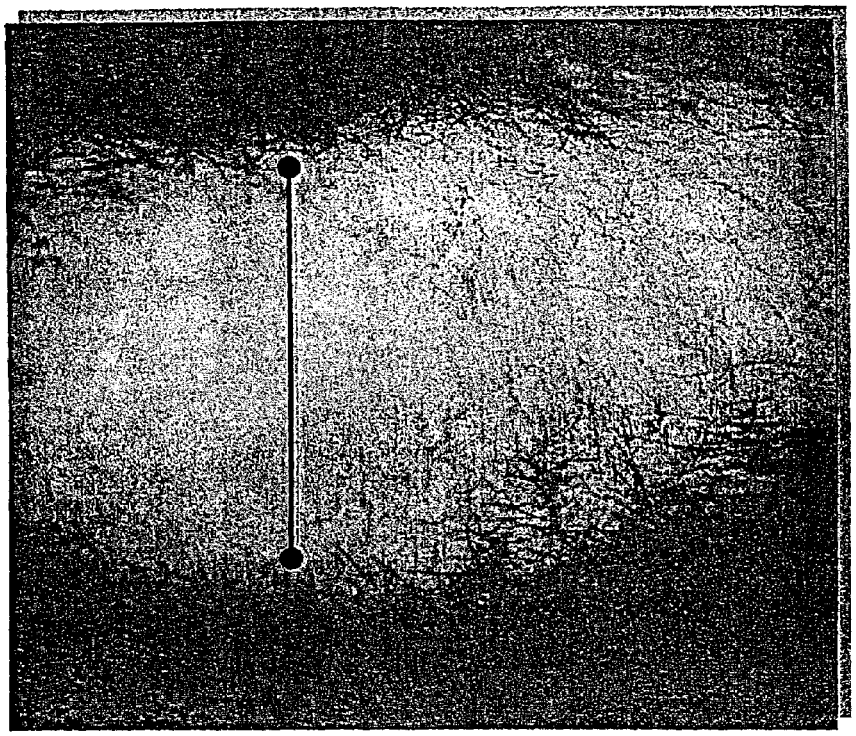
Before Treatment
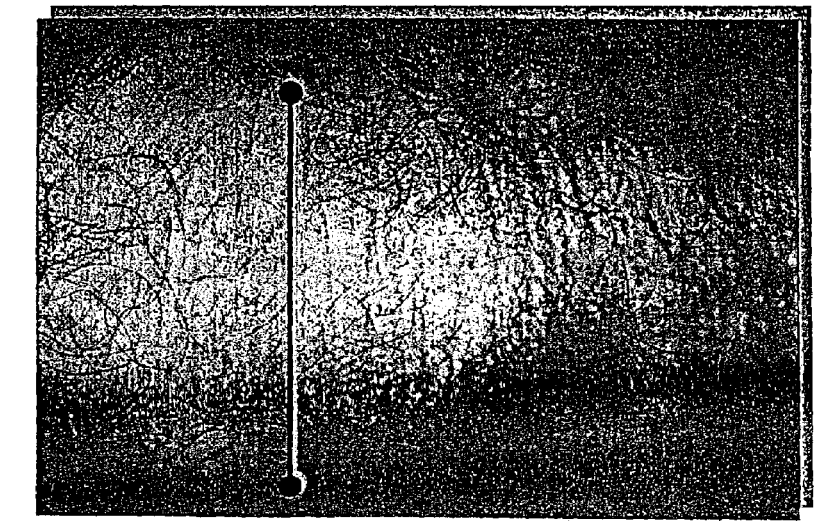

PHARMACEUTICAL AND COSMETIC CARRIER AND COMPOSITION FOR TOPICAL APPLICATION

CROSS REFERENCE TO RELATED APPLICATIONS

This application is a divisional of U.S. patent application Ser. No. 09/653,267, filed on Aug. 31, 2000, which is a utility application claiming priority under 35 U.S.C. §119(e) to U.S. Provisional Patent Application No. 60/216,162, filed on Jul. 3, 2000, all of which applications are hereby incorporated by reference.

FIELD AND BACKGROUND OF THE INVENTION

The present invention relates to a pharmaceutical or cosmetic carrier or composition for topical application onto skin and/or mucosal membranes (e.g., the mucosa of the nose, mouth, eye, ear, vagina or rectum). More particularly, the present invention relates to (i) a cosmetic or pharmaceutical carrier or composition characterized by rheological properties which render the carrier or composition semi-solid at rest and liquid upon application of shear forces (e.g., spread forces) thereto; (ii) methods of preparing same; and (iii) methods of utilizing same for treating a variety of skin or mucosal membrane diseases or disorders.

Most of the skin or mucosal membrane diseases or disorders are the result of inflammation caused by inflammatory agents, such as, but not limited to, bacterial, fungal, viral, parasitic, autoimmune, allergic, hormonal and/or malignant inflammatory agents. The most common skin diseases or disorders include eczema, psoriasis and dermatitis, including contact dermatitis, atopic dermatitis and seborrheic dermatitis.

Eczema and dermatitis result from inflammatory processes that involve the upper dermis and epidermis of the skin. When eczema develops, the keratinocytes in the epidermis distend from one another and fluid is accumulated there amongst in a process known as spongiosis.

In chronic forms of eczema or dermatitis the main change include thickening of the epidermis, which leads to itching, roughening and scaling of the skin surface. The loss of water from the skin leads to inflammation of the horny layer, which later result in cracked and sore skin.

Dermatitis is further classified into contact dermatitis (allergic or non allergic), atopic dermatitis and seborrheic dermatitis.

Non allergic contact dermatitis occurs in response to skin irritants, such as acids, alkalis, oils, detergents and solvents.

Allergic contact dermatitis occurs as a result of sensitization to repeated exposure to an antigen. Allergic contact dermatitis appears in skin areas that were in direct contact with the antigen.

Atopic dermatitis, which affects mainly infants, is characterized by sensitization of the skin to a wide range of common antigens.

Seborrheic dermatitis affects the scalp and other hairy areas, the face, and flexural areas and results from yeast or bacteria induced inflammation. Most people suffer from dandruff which is a mild form of seborrheic dermatitis.

Psoriasis is a dominant autosomal inherited inflammatory disease characterized by enhanced proliferation of keratinocytes which proliferation leads to formation of scaly plaques on, for example, the knees, elbows, buttocks, and which are esthetically unpleasant and cause discomfort to the affected subject.

Skin diseases or disorders are usually treated by creams, gels or ointments containing antifungal agents, steroidal agents and/or antibacterial agents. In many instances such creams, gels and ointments are difficult to spread, result in a greasy and sticky appearance and are usually not appealing for use.

Genital infections are caused by fungal, viral and microbial agents. Genitals infections are treated either systematically, or by the use of creams, ointments or pessaries, which usually leak or otherwise fail to spread well and lead to ineffective therapeutic concentration of the therapeutically active agent(s) therein.

Genital herpes infections are widespread from the 70's and apart from the discomfort they inflict, genital herpes infections may, in some cases, develop into severe disease. Presently, there is no effective medication for genital herpes.

Trichomoniasis is an infection of the urogenital tract caused due to infection by the protozoan *Trichomonas vaginalis*. Trichomoniasis is associated with uncomfort itching and vaginal excretion in women.

Candidiasis is caused by *Candida albicans* and results in itching in the genital area and white discharge therefrom.

Mucosal membrane inflammations can affect other organs such as for example, the eye. Conjuctivitis, caused by different types of bacteria, such as, but not limited to, *Staphylococcus aureus, Streptococcus pneumoniae* or *Haemophilus influenzae*, is generally treated with antibiotic ointments, e.g., bacitracin 500 U/g or gentamicin 0.3 percent ophthalmic ointment instilled into the affected eye. The compliance to these ointments is usually poor due to the sticky feeling they exert.

As is evident from the above descriptions, one of the important routes of administration of a drug for treating a skin or mucosal membrane is by topical application of a drug onto the skin or mucosal membrane. This method is useful for local treatment but it is also possible to apply pessaries via the rectum as an efficient delivery method of systemic agents that are not degraded in the intestine.

Many pharmaceutical carriers are presently known, most of them have disadvantages when topically applied onto the skin or mucosal membranes. For example, when ointments containing petroleum as a carrier are applied onto a skin wound, metabolic products and excreta from the wound cannot be easily removed therefrom because of the difficulty of passing through the hydrophobic petroleum barrier. In addition, the active drug ingredient, which is dissolved or dispersed in the petroleum carrier, is not efficiently absorbed into the wound tissue, thus, the efficacy of the drug is affected. Another example is ophthalmologic ointments, which are applied into the eye, and make the eye area sticky and uncomfortable. Moreover, in physiological aspect, petroleum restricts respiration of a wound tissue and is disturbing to the normal respiration of the skin.

Many groups of drugs including, for example, antibiotic, antifungal, antiinflammatory, anesthetic, analgesic, antiallergic, corticosteroid, retinoid and antiproliferative medications are preferably administered typically using a hydrophobic carrier such as petroleum. However, due to the undesirable consistency of petroleum and similar hydrophobic carriers, their topical use is limited. An additional disadvantage of petroleum-carrier including products relates to the greasy feeling following their topical application to the skin or mucosal membranes.

Besides petroleum, other hydrophobic pharmaceutical carriers are known, including liquid paraffin, lanolin, beeswax, vegetable oil, glycerin monostearate, higher alcohols, polyethylene glycol and some emulsifying agents. All of these agents either suffer the limitations described hereinabove with respect to petroleum or have undesirable (fast) flow properties.

Several hydrophobic liquids, e.g., mono- and poly-unsaturated oils from vegetable and marine sources, silicone oils, mineral oils, and liquid hydrophobic plant-derived oils are known for their therapeutic effects when applied topically. Oils may also contain essential nutritional constituents, such as oil-soluble vitamins (e.g., vitamin A and vitamin E), minerals and other therapeutically effective constituents. Administration of such therapeutic oils in a liquid form does not exert sufficient amounts of the therapeutic agents, because of the oil flow-spread properties. Other examples of therapeutic oils include mineral and silicone oils, which are useful for the treatment of skin dehydration and other medical diseases or disorders. These oils are also liquid at ambient temperature.

There is thus a widely recognized need for, and it would be highly advantageous to have a new pharmaceutical or cosmetic composition or carrier which is semi-solid at rest and which liquefies upon application of shear forces thereto, because such a pharmaceutical or cosmetic composition or carrier can be topically applied as a semi-solid onto an affected area and then turn into a liquid upon spreading, resulting in faster absorption and less greasiness and stickiness.

SUMMARY OF THE INVENTION

According to one aspect of the present invention there is provided a pharmaceutical or cosmetic carrier comprising, by weight, 1–25 percent of a solidifying agent and 75–99 percent of a hydrophobic solvent.

According to another aspect of the present invention there is provided a method of preparing a pharmaceutical or cosmetic carrier, the method comprising the steps of mixing a hydrophobic solvent and a solidifying agent at a temperature above a melting temperature of the solidifying agent so as to obtain a mixture containing 75–99 percent of the hydrophobic solvent by weight and 1–25 percent of the solidifying agent by weight; and cooling the mixture.

According to yet another aspect of the present invention there is provided a pharmaceutical or cosmetic composition comprising, by weight, 1–25 percent of a solidifying agent and 75–99 percent of a hydrophobic solvent, wherein at least one of the solidifying agent and the hydrophobic solvent has a therapeutic or cosmetic beneficial effect.

According to still another aspect of the present invention there is provided a pharmaceutical or cosmetic composition comprising (a) a pharmaceutical or cosmetic carrier containing, by weight, 1–25 percent of a solidifying agent and 75–99 percent of a hydrophobic solvent; and (b) a therapeutically or cosmetically effective amount of a biologically active substance.

According to an additional aspect of the present invention there is provided a method of preparing a pharmaceutical or cosmetic composition, the method comprising the steps of mixing a hydrophobic solvent and a solidifying agent at a temperature above a melting temperature of the solidifying agent so as to obtain a pharmaceutical or cosmetic mixture containing 75–99 percent of the hydrophobic solvent by weight and 1–25 percent of the solidifying agent by weight and further mixing into the mixture a therapeutically or cosmetically effective amount of a biologically active substance.

According to yet an additional aspect of the present invention there is provided a method of treating a disease or disorder of a skin or a mucosal membrane, the method comprising the step of topically administrating to the skin or the mucosal membrane a pharmaceutical or cosmetic composition containing, by weight, 1–25 percent of a solidifying agent and 75–99 percent of a hydrophobic solvent, wherein at least one of the solidifying agent and the hydrophobic solvent has a therapeutic or cosmetic beneficial effect According to a further aspect of the present invention there is provided a method of treating a disease or disorder of a skin or a mucosal membrane, the method comprising the step of topically administrating to the skin or the mucosal membrane a pharmaceutical or cosmetic composition containing (a) a pharmaceutical or cosmetic carrier containing, by weight, 1–25 percent of a solidifying agent and 75–99 percent of a hydrophobic solvent; and (b) a therapeutically or cosmetically effective amount of a biologically active substance.

According to further features in preferred embodiments of the invention described below, the solidifying agent is selected from the group consisting of at least one long chain fatty alcohol having at least 15 carbon atoms in its carbon backbone and at least one fatty acid, having at least 18carbon atoms in its carbon backbone.

According to still further features in the described preferred embodiments the solidifying agent includes a substance selected such that under ambient conditions, the carrier is semi-solid at rest and liquefies upon application of shear forces thereto.

According to still further features in the described preferred embodiments the hydrophobic solvent is selected from the group consisting of at least one marine animal derived oil, at least one terrestrial animal derived oil, at least one mineral oil, at least one silicone oil and at least one plant-derived oil.

According to still further features in the described preferred embodiments the hydrophobic solvent includes an oil selected from the group consisting of olive oil, soybean oil, canola oil, rapeseed oil, cottonseed oil, coconut oil, palm oil, sesame oil, sunflower oil, safflower oil, rice bran oil, borage seed oil, syzigium aromaticum oil, hempseed oil, herring oil, cod-liver oil, salmon oil, corn oil, flaxseed oil, wheat germ oil, rape seed oil, evening primrose oil, rosehip oil, tea tree oil, melaleuca oil and jojova oil.

According to still further features in the described preferred embodiments the hydrophobic solvent includes an oil selected from the group consisting of omega-3 oil and omega-6 oil.

According to still further features in the described preferred embodiments the solidifying agent has at least one alkyl group side chain in its carbon backbone.

According to still further features in the described preferred embodiments the carbon backbone of the fatty acid and/or the fatty alcohol has at least one hydroxyl group at position α or β.

According to still further features in the described preferred embodiments the carbon backbone of the fatty acid or the fatty alcohol has at least one hydroxyl group at positions 8–14.

According to still further features in the described preferred embodiments the solidifying agent includes a 12-hydroxy fatty acid.

According to still further features in the described preferred embodiments at least one of the solidifying agent and the hydrophobic solvent have a therapeutic or cosmetic beneficial effect.

According to still further features in the described preferred embodiments the skin or the mucosal membrane disease or disorder includes inflammation caused by an inflammatory agent selected from the group consisting of a bacterial inflammatory agent, a fungal inflammatory agent, a viral inflammatory agent, a parasitic inflammatory agent, an autoimmune inflammatory agent, an allergic inflammatory agent, a hormonal inflammatory agent and a malignant inflammatory agent.

According to still further features in the described preferred embodiments the skin disease or disorder is selected from the group consisting of psoriasis, acne, seborrhea, seborrheic dermatitis, alopecia and excessive hair growth, itching, wounds, burns, cuts, ulcers, seborrheic dermatitis of the face and trunk, seborrheic blepharitis, contact dermatitis, stasis dermatitis and exfoliative dermatitis.

According to still further features in the described preferred embodiments the statis dermatitis is selected from the group consisting of gravitational eczema, varicose eczema and the exfoliative dermatitis is erythroderma.

According to still further features in the described preferred embodiments the biologically active substance is selected from the group consisting of an antibiotic agent, a free radical generating agent, an antifungal agent, an antiviral agent, a non-nucleoside reverse transcriptase inhibitor, a nucleoside-analog reverse transcriptase inhibitor, a protease inhibitor, a protease inhibitor, a non-steroidal antiinflammatory drug, an immunosuppressant, an antihistamine agent, an antiinflammatory agent, a retinoid agent, a tar agent, an antipruritics agent and a scabicide agent.

According to still further features in the described preferred embodiments (a) the antibiotic agent is selected from the group consisting of chloramphenicol, tetracyclines, synthetic and semi-synthesic penicillins, beta-lactames, quinolones, fluoroquinolnes, macrolide antibiotics, peptide antibiotics, cyclosporines, erytromycin and clinndamycin; (b) the free radical generating agent is benzoyl peroxide; (c) the antifungal agent is selected from the group consisting of azoles, diazole, triazole, miconazole, fluconazole, ketoconazole, clotrimazole, itraconazole griseofulvin, ciclopirox, amorolfine, terbinafine, Amphotericin B and potassium iodide; (d) the antiviral agent is selected from the group of flucytosine (5FC), Vidarabine, acyclovir and Gancyclovir; (e) the nucleoside-analog reverse transcriptase inhibitor is selected from the group consisting of Zidovudine, Stavudine and Lamivudine; (f) the non-nucleoside reverse transcriptase inhibitor is selected from the group consisting of Nevirapine and Delavirdine; (g) the protease inhibitor is selected from the group consisting of Saquinavir, Ritonavir, Indinavir, Nelfinavir, Ribavirin Amantadine, Rimantadine and Interferon; (h) the immunosuppressant is selected from the group consisting of Clobetasol proprionate, Halobetasol proprionate, Betamethasone diproprionate, Betamethasone valerate, Fluocinolone acetonide, Halcinonide, Betamethasone valerate, Fluocinolone acetonide, Hydrocortisone valerate, Triamcinolone acetonide, Hydrocortisone and hexachlorobenzene; (i) the antiinflammatory agent is a vitamin B3 derivative; (j) the retinoid agent is selected from the group consisting of isotretinoin, adapalene and tretinoin; (k) the tar agent is selected from the group consisting of coal tar and cade oil; (l) the antihistamine agent is doxepine hydrochloride; (m) the antipruritic agent is crotampiton; and (n) the scabicide agent is selected from the group consisting of benzyl benzoate, malathion and crotamiton.

According to still further features in the described preferred embodiments the biologically active substance is effective in the treatment of psoriasis, acne, seborrhea, seborrheic dermatitis, alopecia and excessive hair growth, ichthyosis, wounds, burns, cuts, ulcers, psoriasis, seborrheic dermatitis of the face and trunk, seborrheic blepharitis, contact dermatitis, stasis dermatitis or exfoliative dermatitis.

According to still further features in the described preferred embodiments the statis dermatitis is selected from the group consisting of gravitational eczema; varicose eczema, whereas the exfoliative dermatitis is erythroderma.

The present invention successfully addresses the shortcomings of the presently known configurations by providing a biologically active carrier or composition, which is semi solid at rest and liquefies upon application of shear forces thereto, which is therefore easy to spread, highly absorbable, non greasy and non-sticky and which can be used for the treatment of a great number of diseases and syndromes affecting the skin and mucosal membranes.

BRIEF DESCRIPTION OF THE DRAWINGS

The invention is herein described, by way of example only, with reference to the accompanying drawing.

FIG. 1 is a photograph demonstrating the therapeutic effects of a corticosteroid composition prepared in accordance with the teachings of the present invention administered twice a day for 10 days, to a psoriasis patient. The composition was prepared as described in Example 1. The photograph clearly demonstrates a reduction in the psoriatic plaques size following the course of treatment.

DESCRIPTION OF THE PREFERRED EMBODIMENTS

The present invention is of (i) a pharmaceutical or cosmetic carrier or composition for topical application, preferably characterized by Theological properties which render the carrier or composition a semi-solid at rest and a liquid upon application of shear forces thereto; (ii) methods of preparing same; and (iii) methods of utilizing same for treating skin or mucosal membrane diseases or disorders.

The principles and operation of the present invention may be better understood with reference to the accompanying descriptions and examples.

Before explaining at least one embodiment of the invention in detail, it is to be understood that the invention is not limited in its application to the details of composition set forth in the following description or examples. The invention is capable of other embodiments or of being practiced or carried out in various ways. Also, it is to be understood that the phraseology and terminology employed herein is for the purpose of description and should not be regarded as limiting.

According to one aspect of the present invention there is provided a pharmaceutical or cosmetic carrier comprising, by weight, 1–25 percent of a solidifying agent and 75–99 percent of a hydrophobic solvent, which solvent per se is typically liquid at ambient temperature.

As used herein in the specification and in the claims section that follows, the term "carrier" means a base which is, as is defined in the Collins dictionary, the main ingredient of a mixture. Thus, as used herein a "pharmaceutical carrier" is a pharmaceutical base which is used in the preparation of pharmaceutical compositions, whereas a "cosmetic carrier" is a cosmetic base which is used in the preparation of cosmetic compositions.

According to another aspect of the present invention there is provided a method of preparing a pharmaceutical or cosmetic carrier. The method according to this aspect of the invention is effected by mixing a hydrophobic solvent and a solidifying agent at a temperature above a melting temperature of the solidifying agent so as to obtain a mixture containing 75–99 percent of the hydrophobic solvent by weight and 1–25 percent of the solidifying agent by weight; and cooling the mixture, e.g., to room temperature. Preferably, prior to the step of mixing, both the hydrophobic solvent and the solidifying agent are brought to the temperature above the melting temperature of the solidifying agent.

According to still another aspect of the present invention there is provided a pharmaceutical or cosmetic composition comprising, by weight, 1–25 percent of a solidifying agent and 75–99 percent of a hydrophobic solvent, wherein at least one of the solidifying agent and/or the hydrophobic solvent has a therapeutic or cosmetic beneficial effect.

According to yet another aspect of the present invention there is provided a method of preparing a pharmaceutical or cosmetic composition. The method according to this aspect of the invention is effected by mixing a hydrophobic solvent and a solidifying agent at a temperature above a melting temperature of the solidifying agent so as to obtain a mixture containing 75–99 percent of the hydrophobic solvent by weight and 1–25 percent of the solidifying agent by weight; and cooling the mixture, e.g., to room temperature. Preferably, prior to the step of mixing, both the hydrophobic solvent and the solidifying agent are brought to the temperature above the melting temperature of the solidifying agent, e.g., 60–80° C.

Thus, the present invention offers a method of treating a disease or disorder of a skin or a mucosal membrane, such as, but not limited to, a mucosa of a nose, a mucosa of a mouth, a mucosa of an eye, a mucosa of an ear, a mucosa of a vagina and a mucosa of a rectum. The method according to this aspect of the present invention is effected by topically administrating to the skin or the mucosal membrane a pharmaceutical or cosmetic composition containing, by weight, 1–25 percent of a solidifying agent and 75–99 percent of a hydrophobic solvent, wherein at least one of the solidifying agent and the hydrophobic solvent has a therapeutic or cosmetic beneficial effect.

Most preferably, the amount of the solidifying agent in a pharmaceutical or cosmetic carrier according to the present invention is about 4 percent to about 12 percent, whereas the amount of the hydrophobic solvent is about 88 percent to about 96 percent of the total weight of the carrier. As used herein the term about refers to ±20%.

According to a preferred embodiment of the present invention, the solidifying agent includes at least one long chain fatty alcohol having at least 15 carbon atoms in its carbon backbone and/or at least one fatty acid, having at least 18 carbon atoms in its carbon backbone. Preferably, the solidifying agent has at least one alkyl group side chain in its carbon backbone. Additionally or alternatively, the carbon backbone of the fatty acid or the fatty alcohol has at least one hydroxyl group at position α and β. Still additionally or alternatively, the carbon backbone of the fatty acid or the fatty alcohol has at least one hydroxyl group at positions 8–14. According to presently preferred embodiments of the invention, the solidifying agent preferably includes a 12-hydroxy fatty acid.

According to another preferred embodiment of the present invention, the solidifying agent includes a substance selected such that ambient conditions, the carrier is semi-solid at rest and liquefies upon application of shear forces thereto, i.e., has thixotropic properties.

As mentioned above, preferred solidifying agents, according to the present invention, include fatty alcohols having 15 or more carbons in their carbon chain, such as acetyl alcohol and stearyl alcohol (or mixtures thereof). Other examples of fatty alcohols include arachidyl alcohol (C20), behenyl alcohol (C22), 1-triacontanol (C30), as well as alcohols with longer carbon chains (e.g., up to C50). The concentration of the fatty alcohol, required to obtain the thixotropic properties is inversely related to the length of its carbon chains.

Fatty alcohols, derived from beeswax, comprising a mixture of alcohols, where the majority have at least 20 carbon atoms in their carbon chain, are especially suited as solidifying agents according to the present invention.

Another preferred class of solidifying agents includes fatty acids having 18 or more carbons in their carbon chain, such as and stearic acid, arachidic acid (C20), behenic acid (C22), octacosanoic acid (C28), as well as fatty acids with longer carbon chains (e.g., up to C50), or mixtures thereof.

The concentration of the fatty acid required to obtain a thickened carrier is inversely related to the length of its carbon chains. Stearic acid, for example, exerts a considerable thickening effect at about 10 percent concentration, whereas behenic acid would obtain the same thickening effect at a 5 percent concentration.

Optionally, the carbon atom chain of the fatty alcohol or the fatty acid may have at least one double bond.

A further class of solidifying agent according to the present invention comprises long chain fatty alcohols or fatty acids, wherein the carbon atom chain is branched. In an additional preferred class of solidifying agents, the carbon chain of the fatty acid is substituted with a hydroxyl group, e.g., 12 hydroxy stearic acid.

An important property of the fatty alcohols and fatty acids used in context of the carrier and composition of the present invention is related to their therapeutic properties per se. Long chain saturated and mono unsaturated fatty alcohols, e.g., stearyl alcohol, erycyl alcohol, arachidyl alcohol and docosanol have been reported to possess antiviral, antiinfective, antiproliferative and antiinflammatory properties (see, U.S. Pat. No. 4,874,794, which is incorporated herein by reference). Longer chain fatty alcohols, e.g., tetracosanol, hexacosanol, heptacosanol, octacosanol, triacontanol, etc., are also known for their metabolism modifying properties and tissue energizing properties. Long chain fatty acids have also been reported to possess antiinfective characteristics. Thus, the pharmaceutical or cosmetic carrier of the present invention provides an extra therapeutic or cosmetic benefit in comparison with currently used vehicles, such as petroleum, which are inert and non-active.

According to still another preferred embodiment of the present invention, the hydrophobic solvent includes at least one marine animal derived oil, at least one terrestrial animal derived oil, at least one mineral oil, at least one silicone oil and/or at least one plant-derived oil. Examples include, but are not limited to, olive oil, soybean oil, canola oil, rapeseed oil, cottonseed oil, coconut oil, palm oil, sesame oil, sunflower oil, safflower oil, rice bran oil, borage seed oil, syzigium aromaticum oil, hempseed oil, herring oil, cod-liver oil, salmon oil, corn oil, flaxseed oil, wheat germ oil, rape seed oil, evening primrose oil, rosehip oil, tea tree oil, melaleuca oil and/or jojova oil.

As used herein "tea tree oil" or "melaleuca oil" both refer to distillates of the leaves of the Australian tree, *Melaleuca alternifolia*. Tea tree oil is assigned the Chemical Abstract number 68647-73-4 and is commercially available from a variety of sources. Tea tree oil is recognized as having properties as a solvent, antiseptic, antibacterial, antifungal, and pain reliever, as well as other uses. Melaleuca oil has been used in soaps, shampoos, hand creams, tooth pastes, and household cleaners, as well as for treatment of warts and oral candidiasis.

A particularly preferred class of oils to be used in context of the present invention include poly-unsaturated oils which contains omega-3 and omega-6 fatty acids. Thus, in a presently most preferred embodiment of the present invention the carrier contains at least 6 percent omega-3 oil and/or omega-6 oil.

The above described pharmaceutical or cosmetic carrier may be used in the preparation of a pharmaceutical or cosmetic composition comprising (a) a pharmaceutical or cosmetic carrier containing, by weight, 1–25 percent of a solidifying agent and 75–99 percent of a hydrophobic solvent, which is typically liquid at ambient temperature; and (b) a therapeutically or cosmetically effective amount of a biologically active substance. Preferably, at least one of the solidifying agent and the hydrophobic solvent has a therapeutic or cosmetic beneficial effect.

As used herein in the specification and in the claims section that follows the phrase "biologically active substance" refers to an active ingredient which has a therapeutic or cosmetic effect following its administration to an organism (human or animal). The therapeutic or cosmetic effect can be curing, minimizing, preventing or ameliorating a disease or disorder, or improving the physical appearance and aesthetics (e.g., skin hydration) or may have any other therapeutic or cosmetic beneficial effect. The biologically active substance may be, for example, a drug, a vitamin or a vaccine. Thus, the biologically active substances employed in context of the present invention are generally selected from the broad categories of medicaments, agricultural products and cosmetic products. The biologically active substance may be a single drug or a combination of drugs that are dissolved or spread in the carrier of the present invention. Therefore, they are usually, yet not obligatorily, hydrophobic. The concentration of the substance is selected so as to exert its therapeutic or cosmetic effect.

According to another aspect of the invention there is provided a method of preparing a pharmaceutical or cosmetic composition. The method according to this aspect of the present invention is effected by (a) mixing a hydrophobic solvent and a solidifying agent at a temperature above a melting temperature of the solidifying agent so as to obtain a pharmaceutical or cosmetic mixture containing 75–99 percent of the hydrophobic solvent by weight, and 1–25 percent of the solidifying agent by weight; and (b) further mixing into the carrier mixture a therapeutically or cosmetically effective amount of a biologically active substance. Preferably, prior to the step of mixing, both the hydrophobic solvent and the solidifying agent are brought to the temperature above the melting temperature of the solidifying agent, e.g., 60–80° C.

According to a preferred embodiment of this aspect of the present invention the biologically active substance is an antibiotic agent, e.g., chloramphenicol, tetracyclines, synthetic and semi-synthesic penicillins, beta-lactames, quinolones, fluoroquinolnes, macrolide antibiotics, peptide antibiotics, cyclosporines, erytromycin and clinndamycin; a free radical, e.g., benzoyl peroxide; a generating agent; an antifungal agent, e.g., azoles, diazoles, triazoles, miconazole, fluconazole, ketoconazole, clotrimazole, itraconazole griseofulvin, ciclopirox, amorolfine, terbinafine, Amphotericin B and potassium iodide; an antiviral agent, e.g., flucytosine (5FC), Vidarabine, acyclovir and Gancyclovir; a non-nucleoside reverse transcriptase inhibitor, Nevirapine and Delavirdine; a nucleoside-analog reverse transcriptase inhibitor, a protease inhibitor, e.g., e.g., Zidovudine, Stavudine and Lamivudine, a protease inhibitor, e.g., Saquinavir, Ritonavir, Indinavir, Nelfinavir, Ribavirin Amantadine, Rimantadine and Interferon; a non-steroidal antiinflammatory drug, e.g., Voltarene; an immuno, e.g., Clobetasol proprionate, Halobetasol proprionate, Betamethasone diproprionate, Betamethasone valerate, Fluocinolone acetonide, Halcinonide, Betamethasone valerate, Fluocinolone acetonide, Hydrocortisone valerate, Triamcinolone acetonide, Hydrocortisone and hexachlorobenzene; an antihistamine, e.g., doxepine hydrochloride; an antiinflammatory agent, e.g., vitamin B3 or a derivative thereof; a retinoid agent, e.g., isotretinoin, adapalene and tretinoin; a tar agent, e.g., coal tar and cade oil; an antipruritics agent, e.g., crotampiton; or a scabicide agent, e.g., benzyl benzoate, malathion and crotamiton.

The biologically active substance is preferably selected effective in the treatment of a disease or disorder, such as, but not limited to, psoriasis, acne, seborrhea, seborrheic dermatitis, alopecia and excessive hair growth, ichthyosis, wounds, burns, cuts, ulcers, psoriasis, seborrheic dermatitis of the face and trunk, seborrheic blepharitis, contact dermatitis, stasis dermatitis (e.g., gravitational eczema, varicose eczema) or exfoliative dermatitis (e.g., erythroderma).

Thus, the present invention offers another method of treating a disease or disorder of a skin or a mucosal membrane, such as, but not limited to, a mucosa of a nose, a mucosa of a mouth, a mucosa of an eye, a mucosa of an ear, a mucosa of a vagina and mucosa of a rectum. The method is effected by topically administrating thereto a pharmaceutical or cosmetic composition containing (a) a pharmaceutical or cosmetic carrier containing, by weight, 1–25 percent of a solidifying agent and 75–99 percent of a hydrophobic solvent, which is typically liquid at ambient temperature; and (b) a therapeutically or cosmetically effective amount of a biologically active substance.

The pH of the composition or carrier of the present invention is preferably maintained in the range of about pH 5.5–7.0. Acids, bases, and buffers can be used according to methods well known in the art for adjusting the pH of the carrier or composition.

Pharmaceutical compositions manufactured using the carrier according to the present invention are very easy to use. When applied on the afflicted body surface of humans or animals, they are in a semi-solid state, allowing free application without spillage. Upon further application of a mechanical force, e.g., by rubbing the composition onto the body surface, it freely spreads on the surface and is rapidly absorbed. The ease of the application is demonstrated herein in Example 3, where it was compared, in a double blind test to a commercial hydrocortisone preparation. The subjects' score regarding their feeling about the preparation (e.g., the greasiness, stickiness, absorption, penetration, ease of spreading and lack of shiny look) was significantly higher than the score for the commercial preparation.

Additional particulars concerning the use of a variety of biologically active substances in context of the present invention, advantages of the present invention over prior art designs and a variety of applications of the present invention are provided hereinafter.

Treatment of Wounds:

The present invention may find special advantages in the treatment of wounds. Skin wounds which can be treated using the compositions of the present invention include burn wounds, sunburn, cuts, abrasions, acute and chronic wounds and the like. Treatment of burn, ulcers, acute and chronic wounds typically is directed to keeping the wound as clean as possible and making the patient as comfortable as possible. It has been recognized in this respect that keeping the wound moist is advantageous to patient comfort. While maintaining a moist environment will effect some cooling of the tissue, it would be advantageous to be able to decrease the intradermal temperature of a burn wound, which would help to alter the progression of the tissue damage due to heat within the tissues.

Accordingly, it would be advantageous to provide a method for improved treatment of a burn wound that permits significant lowering of the intradermal temperature of the burn wound such that the extent of the burn wound may be limited. Compositions which have antimicrobial agents combined with agents that lead to cooling effect, and which are devoid of adherence to the wound offer relief to people who are suffering from burns or ulcers. The present invention provides a protective moisture barrier to contribute to the sterility of the dressing and to maintain the moistness of the dressing. Sterility is enhanced by the bacteriostatic properties of the wound treatment composition, as well as the shielding action of the barrier's physical presence. An additional barrier to bacteria and contamination is the packaging utilized with the present invention and which is addressed in more detail below.

The wound treatment composition of the present invention comprises as the hydrophobic solvent, for example without limitation, tea tree oil, melaleuca oil and other ingredients in a thixotropic gel formulation. As stated hereinabove, Tea tree oil, or *Melaleuca alternifolia*, is a natural plant extract. The unique wound treatment composition, in addition to creating a moist, soothing environment, is also inherently bacteriostatic. It helps leave the surface of wounds clean and odor free. The odor of chronic wounds is a major concern of health care workers and caregivers. The effectiveness of Melaleuca is increased in the presence of blood and organic material, rather than decreased as is the case with other bacteriostatic products. Melaleuca oil is a natural oil which is considered to be safe and effective on all kinds of cuts and abrasions, surgical wounds, diabetic and mouth ulcers and foot fungi.

The application of the composition of the present invention onto cuts, wounds, burns and ulcers is beneficial both in the cure of an infection or in the protection of the skin from infection. In all such cases, the composition of the present invention is easy to use, being semi-solid when applied and becoming liquid instantly upon rubbing onto the skin.

Suppositories:

For treatment of vaginal infections, suppositories provide an effective mode for administration of a therapeutic agent. Although suppositories have attained some success, they have some disadvantages. Most of the current commercial vaginal suppositories, either melt or dissolve in the vaginal tract into an oily or aqueous liquid. This resulting liquid in turn tends to leak out or is expelled out of the vaginal cavity resulting either in soiled clothing and/or inferior efficacy. Accordingly, it is an object of the present invention to provide an effective antifungal suppository formulation, which overcomes the noted disadvantages associated with the prior art suppositories.

The suppository formulation of the invention is useful in treating vaginal fungus infections in mammalian species, such as humans, cats, dogs and the like. The suppository formulation will be easily inserted into the vaginal cavity and will melt at body temperature soon after insertion. Upon melting, the suppository turns into a gel/cream like consistency, which will adheres to the vaginal membrane thereby providing prolonged duration of effectiveness.

As mentioned above, a pharmaceutical or cosmetic composition in accordance with the teachings of the present invention may include a biologically active substance. The following provides some examples.

Antiviral Agents:

The carrier or composition of the present invention is beneficial in the treatment of viral infections. For example, cold sores are caused by the herpes simplex Type 1 virus and are sometimes referred to as facial herpes. Mollusca are small viral growths that appear singly or in groups on the face, trunk, lower abdomen, pelvis, inner thighs or penis. Shingles (herpes zoster), which usually only occurs once in a lifetime, appears as a rash (clusters of blisters with a red base). It is caused by the same virus responsible for chickenpox. Warts are a common, benign skin tumor caused by viral infection. Eye viral infections, such as viral conjunctivitis is highly contagious and spreads by droplet, fomites, and hand-to-eye inoculation.

Viral infections are currently treated with various antiviral agents, as is summarized in Table 1 below:

TABLE 1

| Antiviral drugs | | |
|---|---|---|
| Drug | Viruses | Chemical Type |
| Vidarabine | Herpesviruses | Nucleoside analog |
| Acyclovir | Herpes simplex (HSV) | Nucleoside analog |
| Gancyclovir | Cytomegalovirus (CMV) | Nucleoside analog |
| Nucleoside-analog reverse transcriptase inhibitors (NRTI): AZT (Zidovudine), ddI (Didanosine), ddC (Zalcitabine), d4T (Stavudine), 3TC (Lamivudine) | Retroviruses (HIV) | Nucleoside analog |
| Non-nucleoside reverse transcriptase inhibitors (NNRTI): Nevirapine, Delavirdine | Retroviruses (HIV) | Nucleoside analog |
| Protease Inhibitors: Saquinavir, Ritonavir, Indinavir, Nelfinavir | HIV | Peptide analog |
| Ribavirin | Broad spectrum: HCV, HSV, measles, mumps, Lassa fever | Triazole carboxamic |

TABLE 1-continued

Antiviral drugs

| Drug | Viruses | Chemical Type |
|---|---|---|
| Amantadine/Rimantadine | Influenza A strains | Tricyclic amine |
| Interferons | Hepatitis B and C | Protein |

It will be appreciated that the intrinsic antiviral effects of the solidifying agents, e.g., fatty alcohols and acids, provides a synergistic effect that will result in a higher therapeutic response.

Antiparasite Agents:

The biologically active substance contained in a composition of the present invention in a therapeutically effective amount may be an antiparasite agent, such as, but not limited to, hexachlorobenzene, carbamate, naturally occurring pyrethroids, permethrin, allethrin, malathion, piperonyl butoxide or mixtures of these drugs.

Antimicrobial Agents:

Antimicrobial agents, also referred to as germicidal agents, which may be used in compositions of the present invention include phenols, including cresols and resorcinols. Antibacterial compositions according to the present invention may be used to treat infections of the skin. An example of a very common skin infection is acne, which involve infestation of the sebaceous gland with *p. acnes*, as well as *Staphylococus aurus* or *Pseudomonas*. Various antibacterial agents have been utilized to treat acne, however, their efficacy is limited due to their low penetration into the hydrophobic environment of the sebaceous gland. The composition of the present invention, being hydrophobic by nature would facilitate an enhanced rate of penetration. Examples of useful antiacne actives include the keratolytics such as salicylic acid (o-hydroxybenzoic acid), derivatives of salicylic acid such as 5-octanoyl salicylic acid, and resorcinol; retinoids such as retinoic acid and its derivatives (e.g., cis and trans); sulfur-containing D and L amino acids and their derivatives and salts, particularly their N-acetyl derivatives, a preferred example of which is N-acetyl-L-cysteine; lipoic acid; antibiotics and antimicrobials such as benzoyl peroxide, octopirox, tetracycline, 2,4,4'-trichloro-2'-hydroxy diphenyl ether, 3,4,4'-trichlorobanilide, azelaic acid and its derivatives, phenoxyethanol, phenoxypropanol, phenoxyisopropanol, ethyl acetate, clindamycin and meclocycline; sebostats such as flavonoids; and bile salts such as scymnol sulfate and its derivatives, deoxycholate and cholate.

The intrinsic antibacterial and antiinflammatory effects of the solidifying agents, i.e., fatty alcohols and acids, of the composition of the present invention provide a combined synergetic effect that results in a better therapeutic response to treatment.

Eye infections are another preferred target for the composition of the present invention. Conjuctivitis, involving bacteria such as *Staphylococcus aureus, Streptococcus pneumoniae*, and *Haemophilus influenzae* is generally treated with antibiotic ointments, e.g., bacitracin 500 U/g or 0.3 percent ophthalmic ointment instilled into the affected eye. Yet, ointment applied into the eye created a sticky feeling and causes major disturbances to the patient. The composition of the present invention, which turns from semi-solid consistency into liquid instantly after application, does not have that disadvantage and thus, treatment compliance is expected to improve. The same advantage is expected when the composition of the present invention is topically applied to mucosal membranes, the oral cavity, the vagina or the rectum.

Another example is parachlorometaxylenol, which is an antimicrobial agent and is suitable for use in the compositions described in the present invention.

Phenols, in concentrations of about 0.2, 1.0, and 1.3 percent by weight are bacteriostatic, bactericidal, and fungicidal, respectively. While it is not intended that the present invention be bound by any particular theory, it is believed that the germicidal action of phenols at these concentrations is effected through protein denaturation. The phenol-protein interaction is relatively weak, allowing the phenol molecule to penetrate deeply into the tissue. Thus, phenol can penetrate relatively dense, intact keratinous matrices, such as the stratum corneum or the nail plate. Several phenol derivatives are more potent than phenol itself, and the most important among these are the halogenated phenols and bis-phenols, the alkyl-substituted phenols and the resorcinols.

Optionally, the present invention may provide a solution for body odors by including hydrophobic antibacterial compounds to help destroy and/or control the amount of bacteria present on the skin, which aids in body odor control.

Hydrophobic antibacterials useful in the present invention include triclosan, triclocarbon, eucalyptol, menthol, methylsalicylate, thymol, and mixtures thereof. Preferred are triclosan and triclocarbon. When included in the composition of the present invention, the hydrophobic antibacterials may be at a level of from about 0.1 percent to about 1.5 percent and preferably from about 0.1 percent to about 0.3 percent, by weight of the composition.

Antifungal Agents:

Fungal infections are another object of treatment using the compositions of the present invention. Superficial fungal infection of the skin is one of the commonest skin disease seen in general practice. Dermatophytosis is probably the most common superficial fungal infection of the skin. It is caused by a group of fungi, which are capable of metabolizing the keratin of human epidermis, nails or hair. There are 3 genera of dermatophytes causing dermatophytosis i.e., microsporum, trichophyton and epidermophyton.

Candidiasis is an infection caused by the yeast like fungus *Candida albicans* or occasionally other species of *Candida*. Clinical syndromes of candidiasis include (a) oral candidiasis (oral thrush); (b) candidiasis of the skin and genital mucous membrane; and (c) *candida paronychia*, which inflicts the nail.

The pharmaceutical composition of the present invention can contain an antifungal drug, which is active against dermatophytes and candida. The drug may include azoles, diazoles, triazoles, miconazole, fluconazole, ketoconazole, clotrimazole, itraconazole griseofulvin, ciclopirox, amorolfine, terbinafine, Amphotericin B, potassium iodide, flucytosine (5FC) and any combination thereof at a therapeutically effective concentration. U.S. Pat. No. 4,352,808 discloses 3-aralkyloxy-2,3-dihydro-2-(1H-imidazolylmethyl)benzo[b]thiophene compounds having antifungal and antibacterial activity.

Steroidal Antiinflammatory Agents:

Suitable steroidal antiinflammatory agents usable in the composition of the present invention may include, although are not limited to, corticosteroids such as hydrocortisone, hydroxyltriamcinolone alphamethyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclarolone acetonide, fludrocortisone, flumethasone pivalate, fluosinolone acetonide, fluocinonide, flucortine butylester, fluocortolone, fluprednidene (fluprednylidene)acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amc, amcinafide, betamethasone and the balance of its esters, chlorprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylproprionate, hydrocortamate, meprednisone, paramethasone, prednisolone, prednisone, beclomethasone dipropionate, betamethasone dipropionate, triamcinolone, and mixtures thereof may be used. The preferred steroidal antiinflammatory for use in the present invention is hydrocortisone.

Table 2 below provides a summary of currently available corticosteroid agent.

TABLE 2

List of steroidal antiinflammatory agents for topical application

| Potency | Compound | Formulation |
| --- | --- | --- |
| Very | Clobetasol proprionate | Cream or ointment 0.05 percent |
| high | Halobetasol proprionate | Cream or ointment 0.05 percent |
| High | Betamethasone diproprionate | Cream or ointment 0.05 percent |
| | Betamethasone valerate | Ointment 0.1 percent |
| | Fluocinolone acetonide | Cream 0.02 percent |
| | Halcinonide | Cream or ointment 0.1 percent |
| Medium | Betamethasone valerate | Cream 0.1 percent |
| | Fluocinolone acetonide | Cream or ointment 0.020 percent |
| | Hydrocortisone valerate | Cream or ointment 0.2 percent |
| | Triamcinolone acetonide | Cream, ointment, or lotion 0.1 percent or 0.020 percent |
| Low | Hydrocortisone | Cream, ointment, or lotion 2.5 percent or 1.0 percent |

Since all corticosteroid drugs are hydrophobic, the carrier of the present invention is most suitable as a vehicle to facilitate an enhanced rate of penetration and better topical distribution thereof.

Furthermore, the intrinsic antiviral, antibacterial and antiinflammatory effects of the solidifying agents, i.e., fatty alcohols and acids, provide a combined synergetic effect that should result in a better therapeutic response to treatment.

Psoriasis is a very common chronic inflammatory skin disease, which may be the target of treatment using a composition of the present invention. Psoriasis is marked by periodic flare-ups of sharply defined red patches covered by a silvery, flaky surface.

Corticosteroid ointments, greasy preparations containing small amount of water, are commonly used for treating psoriasis. Their main disadvantage is in their stickiness, which remains for long time after treatment is over. In this respect it should be noted that the present invention exemplifies the use of a hydrocortisone containing composition that was prepared according to the teachings of the present invention (see Example 1 below). The hydrocortisone preparation was compared to a commercial composition (Example 2) and was shown be highly efficient in the treatment of psoriatic patients. Major reduction in the severity of the disease symptoms, i.e., disappearance of the silvery scales, and reduction of the oedema, erythema and pruritus were observed. Moreover the patients reported that unlike the ointments which are currently available in the market (see Table 2 above), the composition of the present invention was well distributed and absorbed into the skin, without leaving an undesirable greasiness and shiny appearance which characterized the prior art formulations.

Examples of other inflammatory diseases or disorders, which can be treated by the composition of the present invention, wherein the drug is a steroid are: seborrheic dermatitis of the face and trunk, seborrheic blepharitis, contact dermatitis, stasis dermatitis (gravitational eczema; varicose eczema), exfoliative dermatitis (erythroderma), lichen simplex chronicus, pemphigus, conjuctivitis and uveitis.

Topical antihistaminic preparations currently available include 1 percent and 2 percent diphenhydramine (Benadryl® and Caladryl®), 5 percent doxepin (Zonalon®) cream, phrilamine maleate, chlorpheniramine and tripelennamine, phenothiazines, promethazine hydrochloride (Phenergan®) and dimethindene maleate. These drugs, as well as additional antihistamines can also be included in the composition of the present invention.

Additionally, so-called "natural" antiinflammatory agents are useful in context of the present invention. For example, candelilla wax, alpha bisabolol, aloe vera, Manjistha (extracted from plants in the genus *Rubia*, particularly *Rubia cordifolia*), and Guggal (extracted from plants in the genus *Commiphora*, particularly *Commiphora mukul*, may be used as an active ingredient in the composition of the present invention.

Non-Steroidal Antiinflammatory Drugs (NSAIDs):

Another preferred embodiment of the present invention is administration of non-steroidal antiinflammatory drugs (herein NSAIDs) using a composition of the present invention. NSAIDs have been used extensively in recent years for treatment of chronic rheumatic or arthritic conditions and for management of pain. The compounds are believed to bring relief by inhibiting biosynthesis of prostaglandins at affected joints or in other tissue areas. Salicylic acid, or aspirin, and ibuprofen are well-known examples of NSAIDs drugs. Patients using NSAIDs drugs administered orally face an increased risk for peptic ulcers and gastrointestinal blood loss resulting in anemia. Such adverse reactions especially plague patients taking NSAIDs drugs over prolonged periods. Administration of NSAIDs to using the carrier of the present invention will prevent gastrointestinal complications associated with the oral administration of NSAIDs. Such compositions can be used for prolonged treatment of arthritis and other diseases or disorders treated by NSAIDs drugs, while avoiding the gastrointestinal complications associated with oral dose delivery. Application of NSAIDs drugs in a topical composition to the skin of a patient allows a predetermined amount of the NSAIDs drug to be administered continuously to the patient and avoids undesirable effects present with a single or multiple administrations of larger dosages. By maintaining a sustained dosage rate, the NSAIDs drug level in the patient's blood can be better maintained within the optimal therapeutic range Examples of NSAIDs include the following categories: propionic to acid derivatives; acetic acid derivatives; fenamic acid derivatives; biphenylcarboxylic acid derivatives; and oxicams. All of these NSAIDs are fully described in the U.S. Pat. No. 4,985,459 to Sunshine et al. which is incorporated herein by reference. Examples of useful NSAIDs include acetyl salicylic acid, ibuprofen, naproxen, benoxaprofen, flurbiprofen, fenoprofen, fenbufen, ketoprofen, indoprofen, pirprofen, carprofen, oxaprozin, pranoprofen, mniroprofen, tioxaprofen, suprofen, alminoprofen, tiaprofenic acid, fluprofen and bucloxic acid.

Antioxidants/Radical Scavengers:

Suitable antioxidants/radical scavengers useful in context of the present invention include ascorbic acid (vitamin C) and its salts, tocopherol (vitamin E), and its derivatives such as tocopherol sorbate, other esters of tocopherol, butylated hydroxy benzoic acids and their salts, 6-hydroxy-2,5,7,8-tetramethylchroman-2-carboxylic acid (commercially available under the trade name Trolox®), gallic acid and its alkyl esters, especially propyl gallate, uric acid and its salts and alkyl esters, sorbic acid and its salts, the ascorbyl esters of fatty acids, amines (e.g., N,N-diethylhydroxylamine, aminoguanidine), sulfhydryl compounds (e.g., glutathione), and dihydroxy fumaric acid and its salts may be used, as well as EDTA, BHT and the like.

Antibiotics:

Antibiotics which may be used in context of the composition of the present invention, include, but are not limited to, chloramphenicol, tetracyclines, synthetic and semi-synthesic penicillins, beta-lactames, quinolones, fluoroquinolnes, macrolide antibiotics, peptide antibiotics, cyclosporines, erytromycin and clinndamycin.

Topical Anesthetics:

Examples of topical anesthetic drugs useful in context of the composition of the present invention include benzocaine, lidocaine, bupivacaine, chlorprocaine, dibucaine, etidocaine, mepivacaine, tetracaine, dyclonine, hexylcaine, procaine, cocaine, ketamine, pramoxine, phenol, and pharmaceutically acceptable salts thereof.

Retinoi:

Another preferred group of drugs useful in context of the composition of the present invention include retinol, all trans retinoic acid and derivatives, isomers and analogs thereof, collectively termed "retinoids". Compositions according to the present invention, which contain retinoids as the active ingredient can be used for the treatment of acne, seborrea, various dermatoses, inflammation of the skin, mucosal membranes, eye, vagina and the rectum, psoriasis and cancers, by application onto the affected area.

Other Drugs:

As is further detailed hereinunder, it is possible to provide the composition of the present invention onto a dermal patch to generate a transdermal delivery apparatus and applying such patch onto the skin in order to attain effective superficial treatment or enhanced penetration of a drug into the skin or through the skin.

Utilizing such a strategy, one can apply drugs which are currently administered systemically or that require transdermal delivery, in the preferred therapeutic system of the present invention. The following provides some examples for such drugs.

A broad range of analgesics may be utilized including, without limitation, morphine, codeine, heroine, methadone, thebaine, orpiarine, buprenorphine, morphinans, benzomorphans, acetaminophen, butorphanol, diflunisal, fenoprofen, fentanyl, fentanyl citrate, hydrocodone, aspirin, sodium salicylate, ibuprofen, oxymorphone, pentaxicine, naproxen, nalbuphine, mefenamic acid, meperidine and dihydroergotamine.

A typical narcotic antagonist is haloxone. Exemplary antitussive agents include, without limitation, diphenhydramine, guaifenesin, hydromorphone, ephedrine, phenylpropanolamine, theophylline, codeine, noscapine, levopropoxyphene, carbetapentane, chlorpehndianol and benzonatate.

Among the sedatives which may be utilized are, without limitation, chloral hydrate, butabarbital, alprazolam, amobarbital, chlordiazepoxide, diazepam, mephobarbital, secobarbital, diphenhydramine, ethinamate, flurazepam, halazepam, haloperidol, prochlorperazine, oxazepam, and talbutal.

Examples of cardiac drugs are, without limitation, quinidine, propranolol, nifedipine, procaine, dobutamine, digitoxin, phenytoin, sodium nitroprusside, nitroglycerin, verapamil HCl, digoxin, nicardipine HCl, and isosorbide dinitrate.

Antiemetics are illustrated by, without limitation, thiethylperazine, metoclopramide, cyclizine, meclizine, prochlorperazine, doxylamine succinate, promethazine, triflupromazine, and hydroxyzine.

A typical dopamine receptor agonist is bromocriptine mesylate. Exemplary amino acid, peptide and protein hormones include, without limitation, thyroxine, growth hormone (GH), interstitial cell stimulating hormone (ICSH), follicle-stimulating hormone (FSH), thyrotropic hormone (TSH), adrenocorticotropic hormone (ACTH), gonadotropin releasing hormone (GnRH) such as leuprolide acetate, vasopressin and their active degradation products Some products may have sufficiently high molecular weights that absorption through the stratum corneum or mucous membranes may be difficult. Therefore, the invention is applicable only to those hormones which have molecular weights and stereo configurations which will allow passage through the skin.

Female sex hormones which can be used include, without limitations, estradiol, diethylstilbestrol, conjugated estrogens, estrone, norethindrone, medroxyprogesterone, progesterone, and norgestrel.

Typical male sex hormones which may be utilized may be represented by, without limitation, testosterone, methyltestosterone, and fluoxymesterone.

The above listed active permeants may, along with others not specifically disclosed, be used separately or in combination according to the treatment regimen desired.

Cosmetic Agents:

The carrier according to the present invention can also be used to prepare cosmetics for beauty purpose by the addition of skin care agents and perfumes.

Sun Screen Agents:

Also useful in context of the composition of the present invention are sun screening agents. A wide variety of sun screening agents are described in U.S. Pat. No. 5,087,445, to Haffey et al. U.S. Pat. No. 5,073,372, to Turner et al., U.S. Pat. No. 5,073,371, to Turner et al. and Segarin, et al., at Chapter VIII, pages 189 et seq., of Cosmetics Science and Technology all of which are incorporated herein by reference in their entirety. Preferred among those sunscreens which are useful in the composition of the instant invention are those selected from the group consisting of 2-ethylhexyl p-methoxycinnamate, octyl methoxycinnamate, 1-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene) camphor, titanium dioxide, zinc oxide, silica, iron oxide, and mixtures thereof. Still other useful sunscreens are those disclosed in U.S. Pat. Nos. 4,937,370, to Sabatelli and 4,999,186, to Sabatelli et al. These two later references are incorporated by reference herein in their entirety. The sun screening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range. These sun screening agents provide higher efficacy, broader UV absorption, lower skin penetration and longer lasting efficacy relative to conventional sunscreens. Especially preferred examples of these sunscreens include those selected from the group consisting of 4-N,N-(2-ethylhexyl)methylanminobenzoic acid ester of 2,4-hydroxybenzophenone, 4-N,N-(2-ethylhexyl)methylaminobenzoic acid ester with 4-hydroxydibenzoylmethane, 4-N,N-(2-ethylhexyl)methylaminobenzoic acid ester of 2-hydroxy-4-(2-hydroxyethoxy) benzophenone, 4-N,N-(2-ethylhexyl)-methylaminobenzoic acid ester of 4-(2-hydroxyethoxy)dibenzoylmethane, and mixtures thereof. Generally, the sunscreens can comprise from about 0.5 percent to about 20 percent of the compositions useful herein. Exact amounts will vary depending upon the sunscreen chosen and the desired Sun Protection Factor (SPF). SPF is a commonly used measure of photoprotection of a sunscreen against erythema. See Federal Register, Vol. 43, No. 166, pp. 38206–38269, Aug. 25, 1978.

Artificial Tanning Agents and Accelerators:

Examples of artificial tanning agents accelerators which can be used in context of the present invention include dihydroxyacetone, tyrosine, tyrosine esters such as ethyl tyrosinate, and phospho-DOPA.

Reducing Body Odors:

The body fluids includes eccrine sweat, apocrine sweat, sebum, build up of sensible moisture from transepidermal water loss, vaginal discharge, urine, and mixtures thereof. The body odor are odors, which are generated as a result of the natural functioning of a human body. Such odors include, but are not limited to odors produced by microorganisms of the human skin (i.e. bacterial decomposition of skin secretions), urine, or vaginal discharge, and mixtures thereof. The present invention is therefore relevant to a method of reducing body odor comprising the application of a perfume-free, odor-absorbing composition which includes the carrier of the present invention.

Antiwrinkle and Antiskin Atrophy Agents:

Examples of antiwrinkle and antiskin atrophy actives which can be used in context of the present invention include retinoic acid and its derivatives (e.g., cis and trans); salicylic acid and derivatives thereof, sulfur-containing D and L amino acids and their derivatives and salts, particularly the N-acetyl derivatives, a preferred example of which is N-acetyl L-gsteine; thiols, e.g. ethane thiol; alpha-hydroxy acids, e.g. glycolic acid, and lactic acid; phytic acid, lipoic acid; lysophosphatidic acid, and skin peel agents (e.g., phenol and the like).

Excipients and Additional Agents:

The pharmaceutical or cosmetic composition of the present invention may further include a variety of pharmaceutical or cosmetic ingredients, which are added in order to fine-tune the consistency of the formulation, protect the formulation components from degradation and oxidation and bestow their cosmetic acceptability. Such excipients, may be selected from the group consisting of water, surfactants, emulsifiers, diglycerides, triglycerides, stabilizing agents, antioxidants, glycerol, ethanol, propanol, isopropanol, butanol, polymeric gelling agents, flavoring, colorant and odorant agents and other formulation components, used in the art of pharmaceutical and cosmetic formulary.

Additional active and inactive ingredients may also include, without limitation, local analgesics such as benzocaine, menthol, and the like (wherein menthol is also capable of providing a soothing, cooling sensation), as well emollients, antihistamines, fragrances, thickeners and preservatives other than those already listed.

Emollients:

The compositions of the present invention can also include an emollient. Emollient is used to smooth the surface of the skin. Examples of suitable emollients include, but are not limited to, volatile and non-volatile silicone oils (e.g., dimethicone, cyclomethicone, dimethiconol, and the like), highly branched hydrocarbons, and mixtures thereof. Emollients useful in the instant invention are further described in U.S. Pat. No. 4,919,934, to Deckner et al., which is incorporated herein by reference in its entirety. The emollients can typically comprise in total from about 0.1 percent to about 25 percent, more preferably from about 0.5 percent to about 10 percent, and most preferably from about 0.5 percent to about 5 percent by weight of the composition.

A variety of additional ingredients can be incorporated into the composition of the present invention. Non-limiting examples of these additional ingredients include vitamins and derivatives thereof (e.g. tocopherol, panthenol, and the like); other thickening agents (e.g., polyacrylamide and $C_{13}$–$C_{14}$ isoparaffin and laureth-7, available as Sepigel 305 from Seppic Corp., Fairfield, N.J.; and branched polysaccharides such as scleroglucan available under the tradename Clearogel® CS 11 from Michel Mercier Products Inc., Mountainside, N.J.); saturated and/or unsaturated alkyl alpha hydroxy acids; resins; gums (e.g. guar gum, xanthan gum and the like); waxes (both naturally occurring and synthetic); polymers for aiding the film-forming properties and substantivity of the composition (such as a copolymer of eicosene and vinyl pyrrolidone, an example of which is available from GAF Chemical Corporation as Ganex V-220®); abrasive scrub particles for cleansing and exfoliating the skin, e.g., ACuscrub® Mild Abrasives (e.g., ACuscrub® 30, 31, 32, 40, 41, 42, 43, 44, 50, 51, and 52) available from Allied Signal, Inc., Morristown, N.J.; and 3M Brand PMU Capsules microencapsulated mineral oil available from 3M Corporation, St. Paul, Minn.!; preservatives for maintaining the antimicrobial integrity of the compositions; skin penetration aids such as DMSO, 1-dodecylazacycloheptan-2-one (available as Azone® from the Upjohn Co.) and the like; skin bleaching (or lightening) agents including but not limited to hydroquinone, kojic acid and sodium metabisulfite; chelators and sequestrants; and aesthetic components such as fragrances, pigments, colorings, essential oils, skin sensates, astringents, skin soothing agents, skin healing agents and the like, nonlimiting examples of these aesthetic components include panthenol and derivatives (e.g. ethyl panthenol), aloe vera, pantothenic acid and its derivatives, clove oil, menthol, camphor, eucalyptus oil, eugenol, menthyl lactate, witch hazel distillate, allantoin, bisabalol, dipotassium glycyrrhizinate and the like.

The carrier system may also comprise, when desired, a suitable gelling agent including, but not limited to, cellulose esters such as hydroxypropyl cellulose (Klucel®), hydroxyethyl cellulose (Natrosol®), polyvinylpyrrolidone (Povidone®), carboxyvinyl polymer (HIVIS 105®) and the like that may be provided in any amount necessary to thicken the composition to a desired gel consistency. When formulated as a gel, the base composition exhibits favorable spreadability characteristics. In addition, it remains visible on the skin surface longer, thereby instilling in the user the impression that the vehicle is more completely delivering its active ingredient(s).

In addition to the aforementioned ingredients, it should also be noted that the following ingredients may also be included in the inventive composition, as desired: coloring agents, fragrances, conditioners, moisturizers, surfactants, antioxidants, preservatives, etc.

Preferred ingredients are saturated and/or unsaturated alkyl alpha hydroxy acids, at a level of from about 0.05 percent to about 5 percent by weight of the composition, such as lactic acid, lactate salts (e.g., ammonium and quaternary alyl ammonium), glycolic acid, glycolate salts (e.g., ammonium and quaternary allyl ammonium), and fruit acids. A discussion of alpha hydroxy acids is disclosed in Walter P. Smith, Hydroxy Acids and Skin Aging, Soap/Cosmetics/Chemical Specialties. pp. 54–59, (September 1993), which is herein incorporated by reference in its entirety.

Preservatives:

Antimicrobial preservatives useful in the present invention include biocidal and biostatic compounds (substances that kill microorganisms and/or regulate the growth of microorganisms). Suitable antimicrobial preservatives have a solubility of 0.3 percent or greater. In addition, suitable preservatives are those which can come into contact with skin without high irritation potential. Preservatives suitable for use in the present compositions are described in U.S. Pat. No. 5,534,165, to Pilosof et al.

It is preferable to use a broad spectrum preservative such as one that is effective both on bacteria (both gram positive and gram negative) and fungi. A limited spectrum preservative such as one that is only effective on a single group of microorganisms, for example fungi, can be used in combination with a broad spectrum preservative or other limited spectrum preservatives with complimentary and/or supplementary activity. A mixture of broad spectrum preservatives can also be used.

Colorants and Dyes:

Colorants and dyes can be optionally added to the odor absorbing compositions for visual appeal and performance impression. When colorants are used, care must be taken in the selection of choosing dyes that will not color skin. Preferred colorants for use in the present compositions are highly water-soluble dyes, e.g., acid blue 3, acid blue 104, acid green 1, acid green 25, acid yellow 3, acid yellow 73 sodium salt, D&C green No. 5, 6 & 8, D&C yellow No. 7, 8, 10 & 11, D&C violet No. 2, FD&C blue No. 1 & 2, FD&C green No. 3, FD&C yellow No. 5 & 6, and mixtures thereof.

Other Optional Ingredients:

The composition of the present invention can optionally contain adjunct odor-controlling materials, such as zinc salts, cationic polymers, anionic polymers, carbonate salts, bicarbonate salts, zeolites, and activated carbon; chelating agents; colorants; and/or antiperspirants.

Optionally, the composition of the present invention can include zinc salts for added odor absorption and/or antimicrobial benefit for the cyclodextrin solution. Zinc compounds have been used most often for their ability to ameliorate malodor, e.g., in mouth wash products, as disclosed in U.S. Pat. No. 4,325,939 and U.S. Pat. No. 4,469,674 to Shah, et al. Highly-ionized zinc salts, such as zinc chloride, provide the best source of zinc ions. The zinc salt, zinc phenolsulfonate, is preferred for use in the skin composition of the present invention; although others may also fall within the scope of the present invention. However, care must be taken in selecting zinc salts, as well as their levels, since some may be irritants to the skin and they are not preferred for use in the present invention.

Administration via Dermal Patch:

The compositions of the present invention may also be delivered to the skin using conventional dermal-type patches or articles, wherein the active ingredients composition is contained within a laminated structure, that serves as a drug delivery device to be affixed to the skin. In such a structure, the active ingredients composition is contained in a layer, or "reservoir", underlying an upper backing layer. The laminated structure may contain a single reservoir, or it may contain multiple reservoirs. In one embodiment, the reservoir comprises a polymeric matrix of a pharmaceutically acceptable contact adhesive material that serves to affix the system to the skin during active ingredients delivery. Examples of suitable skin contact adhesive materials include, but are not limited to, polyethylenes, polysiloxanes, polyisobutylenes, polyacrylates, polyurethanes, and the like. The particular polymeric adhesive selected will depend on the particular active ingredients, vehicle, etc., i.e., the adhesive must be compatible with all components of the active ingredients-containing composition. Alternatively, the active ingredients-containing reservoir and skin contact adhesive are present as separate and distinct layers, with the adhesive underlying the reservoir which, in this case, may be either a polymeric matrix as described above, or it may be a liquid or hydrogel reservoir, or may take some other form.

The backing layer in these laminates, which serves as the upper surface of the device, functions as the primary structural element of the laminated structure and provides the device with much of its flexibility. The material selected for the backing material should be selected so that it is substantially, impermeable to the active ingredients and to any other components of the active ingredients-containing composition, thus preventing loss of any components through the upper surface of the device. The backing layer may be either occlusive or nonocclusive, depending on whether it is desired that the skin become hydrated during active ingredients delivery. The backing is preferably made of a sheet or film of a preferably flexible elastomeric material. Examples of polymers that are suitable for the backing layer include polyethylene, polypropylene, and polyesters.

During storage and prior to use, the laminated structure includes a release liner. Immediately prior to use, this layer is removed from the device to expose the basal surface thereof, either the active ingredients reservoir or a separate contact adhesive layer, so that the system may be affixed to the skin. The release liner should be made from a active ingredients/vehicle impermeable material.

Such devices may be fabricated using conventional techniques, known in the art, for example by casting a fluid admixture of adhesive, active ingredients and vehicle onto the backing layer, followed by lamination of the release liner. Similarly, the adhesive mixture may be cast onto the release liner, followed by lamination of the backing layer. Alternatively, the active ingredients reservoir may be prepared in the absence of active ingredients or excipient, and then loaded by "soaking" in a active ingredients/vehicle mixture.

Therapeutic Effect and Dosage:

The therapeutic efficacy of the compositions described herein can be determined by standard pharmaceutical procedures in experimental animal models or human beings. The data obtained from these studies can be used in formulating a range of dosage for use in human (See e.g., Fingl, et al., 1975, in "The Pharmacological Basis of Therapeutics", Ch. 1 p.1).

The effective concentration of the drug is calculated by procedures known in the art that can be employed to determine the effective local concentration. For example, corticosteroid induced vasoconstriction in man may provide a preliminary useful hint to topical antiinflammatory activity.

The amount of a composition to be administered will, of course, be dependent on the subject being treated, the severity of the affliction, the manner of administration, the judgment of the prescribing physician, etc.

Short term studies over one or two weeks may not be the only relevant investigation for the clinical comparison of the topical drugs. In practice these are sometimes applied over long periods of time and the differences may be apparent only after months of treatment. For this reason, depending on the novelty of the product and the indications claimed, certain studies of efficacy as well as of safety will be required.

Since the hydrophobic agent can be derived from a biological source, it is necessary to assess the repeatability of the therapeutic effect as well as the reproducibility, the specificity and the accuracy of the agent. This should be done by an analytical chemistry laboratory which is defined as GLP (Good Laboratory Practice).

Compositions of the present invention may, if desired, be presented in a bottle or jar or other container approved by the FDA, which may contain one or more unit dosage forms containing the active ingredient. Compositions such as those described in the present invention may be particularly susceptible to microbial and other contamination, and special measures need to be taken to prevent any contamination. The pack or dispenser may also be accompanied by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition. Suitable conditions indicated on the label may include treatment for acne or for psoriasis and is the like.

The Gist and Advantages of the Present Invention Over the Prior Art:

The gist of the present invention is based on the striking discovery that the addition of fatty alcohols to hydrophobic liquids, such as saturated, mono-unsaturated or poly-unsaturated oils, as well as mineral and silicone oils, may alter the physicochemical properties of the material, including the solidification thereof. This appears to be particularly relevant when the fatty alcohol has a molecular weight greater than 200 Da and at least one hydroxyl group in its chemical structure. The addition of a fatty alcohol to a liquid oil also gives rise to thixotropic properties (e.g., being semi-solid at rest and liquid upon application of shear forces thereto). This property enables application of a thixotropic mixture as a semi-solid state to a body surface, which subsequently becomes substantially liquid and therefore more spreadable and penetrable when rubbed onto the body surface. Thus, one of the most important properties of the carrier and composition of the present invention is that they are semi-solid at rest and that they liquefy upon application of shear forces thereto. Semi-solid hydrophobic formulations are important not only for the pharmaceutical market but also for cosmetic products, such as carriers of sunscreen compounds, oil-soluble plant extracts, materials for scrubbing purposes and other active and non-active cosmetic ingredients. Unlike aqueous liquids, which are rather easy to solidify due to their hydrogen bond forming ability, oils are difficult to solidify. Several methods have been proposed to increase the viscosity of oils. Various gelling agent, such as inorganic complexing agents (U.S. Pat. No. 4,780,309), hydrocolloids (U.S. Pat. No. 4,576,645), polymers and copolymers (U.S. Pat. No. 5,985,821; 5,925,707), polysaccharides (U.S. Pat. No. 5,961,998) have been previously described in the context of solidifying oils for use in food and cosmetics. The use of waxes, fatty alcohols, fatty acids and 12 hydroxy stearic acid in solidifying waste oils, in order to facilitate the removal of such oils have also been described (JP-A-112385/1979; JP-A-106298/1980). U.S. Pat. No. 5,817,322 teaches pharmaceutical compositions, comprising an oil and beeswax as a gelling agent, which form a netted framework of the beeswax and form a film after application on a body surface.

However, the prior art fails to teach a carrier or composition for topical application which is semi-solid at rest and which liquefies upon application of shear forces thereto.

EXAMPLES

Additional objects, advantages, and novel features of the present invention will become apparent to one ordinarily skilled in the art upon examination of the following examples, which are not intended to be limiting. Additionally, the various embodiments and aspects of the present invention as delineated hereinabove and as claimed in the claims section below finds experimental support in the following examples.

Example 1

Preparation of a Corticosteroid Composition

Stearyl alcohol (60 grams) was heated to 80° C. USP olive oil (940 grams) was heated to the same temperature. While at 80° C., the stearyl alcohol was added to the preheated olive oil. 20 grams glycerin, 20 grams tri-stearin, 1 gram of an antioxidant mixture were added by agitation. 1 gram of betamethasone valerate was added and the mixture was poured into containers (5 gram tubes) and was allowed to cool spontaneously. While the mixture cooled to ambient temperature it gradually turned into a semi-solid.

Example 2

Efficacy of the Corticosteroid Composition for the Treatment of Psoriasis

In a preliminary experiment, five patients with psoriasis were treated with the corticosteroid preparation described in Example 1, twice a day, for 10 days. In three out of five patients the psoriatic plaques and skin thickness were significantly reduced after 7–10 days of treatment (FIG. 1). The forth patient had a moderate improvement and fifth showed only mild response to the treatment.

Example 3

A Double Blind Comparative Study Between the Corticosteroid Composition and a Conventional Ointment Eight subjects were requested to apply 1 gram of the corticosteroid composition described in Example 1 on one arm and 1 gram of commercial betamethasone valerate ointment, on the other arm. The study was performed in a double blind manner. The subjects had to describe their opinion about the ease of application, ease of spreading, spreadability and penetrability of each of the products and to give their scores on a scale of 0 to 3 (0=poor; 1=barely acceptable; 2=acceptable and 3=excellent).

As can be clearly seen in Table 3 below, the corticosteroid composition of Example 1 obtained higher score in each of the study parameters.

TABLE 3

Comparison between the corticosteroid composition and Betamethasone commercial ointment

| Parameters | Corticosteroid Composition (Example 1) mean Score | Commercial Betamethasone valerate ointment mean Score |
| --- | --- | --- |
| Ease of application | 2.5 | 1.8 |
| Ease of spreading | 2.4 | 1.8 |
| Spreadability | 2.8 | 1.6 |
| Penetrability | 2.4 | 2.0 |
| Lack of stickiness | 2.6 | 1.0 |
| Lack of greasiness | 2.6 | 0.8 |
| Lack of shiny look | 1.9 | 1.4 |
| Overall rating | 2.6 | 1.6 |

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of treating a disease or disorder of a skin or a mucosal membrane comprising:
   topically administering to the skin or the mucosal membrane a pharmaceutical composition containing, by weight, 1–25 percent of a solidifying agent, wherein the solidifying agent consists essentially of at least one long chain fatty alcohol having at least 15 carbons atoms in its carbon backbone and at least one fatty acid, having at least 18 carbon atoms in its carbon backbone, and 75–99 percent of a hydrophobic solvent, wherein at least one of the solidifying agent and the hydrophobic agent has a therapeutic or cosmetic beneficial effect, and wherein the solidifying agent and the hydrophobic solvent are selected such that under ambient conditions, the composition is semi-solid a rest and liquefies upon application of shear forces thereto,
   wherein the disease or disorder is selected from the group consisting of psoriasis, acne, seborrhea, seborrheic dermatitis, alopecia and excessive hair growth, ichthyosis, wounds, burns, cuts, ulcers, psoriasis, seborrheic dermatitis of the face and trunk, seborrheic blepharitis, contact dermatitis, stasis dermatitis and exfoliative dermatitis.

2. The method of claim 1, wherein the statis dermatitis is selected from the group consisting of gravitational eczema, varicose eczema and further wherein the exfoliative dermatitis is erythroderma.

3. The method of claim 1, wherein the mucosal membrane is selected from the group consisting of a mucosa of a nose, a mucosa of a mouth, a mucosa of an eye, a mucosa of an ear, a mucosa of a vagina and a mucosa of a rectum.

4. The method of claim 1, wherein the disease or disorder is an inflammation caused by an inflammatory agent selected from the group consisting of a bacterial inflammatory agent, a fungal inflammatory agent, a viral inflammatory agent, a parasitic inflammatory agent, an autoimmune inflammatory agent, an allergic inflammatory agent, a hormonal inflammatory agent and a malignant inflammatory agent.

5. The method of claim 1, wherein the hydrophobic solvent is selected from the group consisting of marine animal derived oils, terrestrial animal derived oils, mineral oils, silicone oils and plant-derived oils.

6. The method of claim 1, wherein the hydrophobic solvent includes an oil selected from the group consisting of olive oil, soybean oil, canola oil, rapeseed oil, cottonseed oil, coconut oil, palm oil, sesame oil, sunflower oil, safflower oil, rice bran oil, borage seed oil, syzigium aromaticum oil, hempseed oil, herring oil, cod-liver oil, salmon oil, corn oil, flaxseed oil, wheat germ oil, rape seed oil, evening primrose oil, rosehip oil, tea tree oil, melaleuca oil and jojova oil.

7. The method of claim 1, wherein the hydrophobic solvent includes an oil selected from the group consisting of omega-3 oil and omega-6 oil.

8. The method of claim 1, wherein at least one of the fatty alcohol and the fatty acid has at least one alkyl group side chain in its carbon backbone.

9. The method of claim 1, wherein the carbon backbone of at least one of the fatty acid and fatty alcohol has at least one hydroxyl group.

10. The method of claim 9, wherein the carbon backbone of at least one of the fatty acid and the fatty alcohol has at least one hydroxyl group at positions 8–14.

11. The method of claim 1, wherein the solidifying agent includes a 12-hydroxy fatty acid.

12. A method of treating a disease or disorder of a skin or a mucosal membrane comprising the step of topically administrating thereto a pharmaceutical composition containing:
   (a) a pharmaceutical or cosmetic carrier containing, by weight, 1–25 percent of a solidifying agent, wherein the solidifying agent consists essentially of at least one long chain fatty alcohol having at least 15 carbon atoms in its carbon backbone and at least one fatty acid having at least 18 carbon atoms in its carbon backbone, and 75–99 percent of a hydrophobic solvent; and
   (b) a therapeutically or cosmetically effective amount of a biologically active substance,
   wherein the solidifying agent and the hydrophobic solvent are selected such that under ambient conditions, the carrier is semi-solid at rest and liquefies upon application of shear forces thereto, and
   wherein the biologically active substance is effective in the treatment of a disease or disorder selected from the group consisting of psoriasis, acne, seborrhea, seborrheic dermatitis, alopecia and excessive hair growth, ichthyosis, wounds, burns, cuts, ulcers, psoriasis, seborrheic dermatitis of the face and trunk, seborrheic blepharitis, contact dermatitis, stasis dermatitis and exfoliative dermatitis.

13. The method of claim 12, wherein the mucosal membrane is selected from the group consisting of a mucosa of a nose, a mucosa of a mouth, a mucosa of an eye, a mucosa of an ear, a mucosa of a vagina and mucosa of a rectum.

14. The method of claim 12, wherein the hydrophobic solvent is selected from the group consisting of marine animal derived oils, terrestrial animal derived oils, mineral oils, silicone oils and plant-derived oils.

15. The method of claim 12, wherein the hydrophobic solvent includes an oil selected from the group consisting of olive oil, soybean oil, canola oil, rapeseed oil, cottonseed oil, coconut oil, palm oil, sesame oil, sunflower oil, safflower oil, rice bran oil, borage seed oil, syzigium aromaticum oil, hempseed oil, herring oil, cod-liver oil, salmon oil, corn oil, flaxseed oil, wheat germ oil, rape seed oil, evening primrose oil, rosehip oil, tea tree oil, melaleuca oil and jojova oil.

16. The method of claim 12, wherein the hydrophobic solvent includes an oil selected from the group consisting of omega-3 oil and omega-6 oil.

17. The method of claim 12, wherein at least one of the fatty acid and the fatty alcohol has at least one alkyl group side chain in its carbon backbone.

18. The method of claim 12, wherein the carbon backbone of at least one of the fatty acid and the fatty alcohol has at least one hydroxyl group.

19. The method of claim 12, wherein the carbon backbone of at least one of the fatty acid and the fatty alcohol has at least one hydroxyl group at positions 8–14.

20. The method of claim 12, wherein the solidifying agent comprises a 12-hydroxy fatty acid.

21. The method of claim 12, wherein the disease or disorder is inflammation caused by an inflammatory agent selected from the group consisting of a bacterial inflammatory agent, a fungal inflammatory agent, a viral inflammatory agent, a parasitic inflammatory agent, an autoimmune inflammatory agent, an allergic inflammatory agent, a hormonal inflammatory agent and a malignant inflammatory agent.

22. The method of claim 12, wherein the statis dermatitis is selected from the group consisting of gravitational eczema, varicose eczema and further wherein the exfoliative dermatitis is erythroderma.

23. The method of claim 12, wherein the biologically active substance is effective in the treatment of a disease or disorder selected from the group consisting of psoriasis, acne, seborrhea, seborrheic dermatitis, alopecia and excessive hair growth, ichthyosis, wounds, burns, cuts, ulcers, psoriasis, seborrheic dermatitis of the face and trunk, seborrheic blepharitis, contact dermatitis, stasis dermatitis and exfoliative dermatitis.

24. The method of claim 23, wherein the statis dermatitis is selected from the group consisting of gravitational eczema, varicose eczema and further wherein the exfoliative dermatitis is erythroderma.

25. The method of claim 12, wherein the biologically active substance is selected from the group of consisting of an antibiotic agent, a free radical generating agent, an antifungal agent, an antiviral agent, a non-steroidal antiinflammatory drug, an immunosuppressant, an antihistamine agent, an antiinflammatory agent, a retinoid agent, a tar agent, an antipruritics agent and a scabicide agent.

26. The method of claim 25, wherein:
(a) the antibiotic agent is selected from the group consisting of chloramphenicol, tetracyclines, synthetic and semi-synthesic penicillins, beta-lactames, quinolones, fluoroquinolnes, macrolide antibiotics, peptide antibiotics, cyclosporines, erytromycin and clinndamycin;
(b) the free radical generating agent is benzoyl peroxide;
(c) the antifungal agent is selected from the group consisting of azoles, diazoles, triazoles, miconazole, fluconazole, ketoconazole, clotrimazole, itraconazole griseofulvin, ciclopirox, amorolfine, terbinafine, Amphotericin B and potassium iodide;
(d) the antiviral agent is selected from the group consisting of flucytosine (5FC), Vidarabine, acyclovir and Gancyclovir;
(e) the immunosuppressant is selected from the group consisting of Clobetasol proprionate, Halobetasol proprionate, Betamethasone diproprionate, Betamethasone valerate, Fluocinolone acetonide, Halcinonide, Betamethasone valerate, Fluocinolone acetonide, Hydrocortisone valerate, Triamcinolone acetonide, Hydrocortisone and hexachlorobenzene;
(f) the antiinflammatory agent is a vitamin B3;
(g) the retinoid agent is selected from the group consisting of isotretinoin, adapalene and tretinoin;
(h) the tar agent is selected from the group consisting of coal tar and cade oil;
(i) the antihistamine agent is doxepine hydrochloride;
(j) the antipruritic agent is crotampiton; and
(k) the scabicide agent is selected from the group consisting of benzyl benzoate, malathion and crotamiton.

27. A method of treating dermatosis of a skin or a mucosal membrane comprising the step of topically administering to the skin or the mucosal membrane a pharmaceutical or cosmetic composition containing,
(a) a carrier comprising, by weight, 1–12 percent of a solidifying agent consisting essentially of long chain fatty alcohols having 18–22 carbons atoms in its carbon backbone and long chain fatty acids having 18–22 carbon atoms in its carbon backbone and 75–99 percent of a triglyeride hydrophobic solvent; and
(b) a therapeutic or cosmetically effective amount of a biologically active substance that treats a symptom of dermatosis.

28. The method of claim 27, wherein the dermatosis is an inflammation caused by a fungal inflammatory agent.

29. The method of claim 27, wherein the biologically active agent is an antimicrobial agent.

\* \* \* \* \*

UNITED STATES PATENT AND TRADEMARK OFFICE
CERTIFICATE OF CORRECTION

PATENT NO. : 6,994,863 B2
APPLICATION NO. : 10/392071
DATED : February 7, 2006
INVENTOR(S) : Meir Eini et al.

Page 1 of 1

It is certified that error appears in the above-identified patent and that said Letters Patent is hereby corrected as shown below:

Col. 25, line 66, delete "a" before the word rest, insert -- at --
Col. 28, line 11, delete "synthesic" insert -- synthetic --

Signed and Sealed this

Twelfth Day of September, 2006

JON W. DUDAS
*Director of the United States Patent and Trademark Office*